US010046032B2

(12) United States Patent
Atarot et al.

(10) Patent No.: US 10,046,032 B2
(45) Date of Patent: Aug. 14, 2018

(54) USE OF INSULIN FOR PROMOTING GASTRIC EMPTYING

(71) Applicant: NUTRINIA LTD., Nazareth Illit (IL)

(72) Inventors: Tal Atarot, Tel-Mond (IL); Michal Olshansky, Tel-Aviv (IL)

(73) Assignee: Nutrinia, LTD., Nazareth Illit (IL)

( * ) Notice: Subject to any disclaimer, the term of this patent is extended or adjusted under 35 U.S.C. 154(b) by 0 days.

(21) Appl. No.: 15/468,965

(22) Filed: Mar. 24, 2017

(65) Prior Publication Data

US 2017/0319663 A1    Nov. 9, 2017

Related U.S. Application Data

(60) Provisional application No. 62/312,473, filed on Mar. 24, 2016.

(51) Int. Cl.
| | |
|---|---|
| *A61K 9/00* | (2006.01) |
| *A61K 38/00* | (2006.01) |
| *A61K 47/00* | (2006.01) |
| *A61K 38/28* | (2006.01) |
| *A61K 47/36* | (2006.01) |

(52) U.S. Cl.
CPC ............ *A61K 38/28* (2013.01); *A61K 9/0053* (2013.01); *A61K 47/36* (2013.01)

(58) Field of Classification Search
CPC ....... A61K 38/28; A61K 47/36; A61K 9/0053
See application file for complete search history.

(56) References Cited

U.S. PATENT DOCUMENTS

| | | | |
|---|---|---|---|
| 4,832,967 A | 5/1989 | Autant | |
| 4,944,944 A | 7/1990 | Tang et al. | |
| 5,013,569 A | 5/1991 | Rubin | |
| 5,279,832 A | 1/1994 | Greissinger | |
| 5,356,625 A | 10/1994 | Ying | |
| 5,418,010 A | 5/1995 | Janda | |
| 5,531,989 A | 7/1996 | Paul | |
| 5,545,410 A | 8/1996 | Fox | |
| 6,048,562 A | 4/2000 | Mandralis | |
| 6,365,177 B1 | 4/2002 | Shehadeh | |
| 6,399,090 B1 | 6/2002 | Shehadeh | |
| 6,482,517 B1 | 11/2002 | Anderson | |
| 6,548,043 B1 | 4/2003 | Wagner et al. | |
| 6,797,293 B2 | 9/2004 | Shin | |
| 6,989,195 B2 | 1/2006 | Anderson | |
| 8,026,211 B2 | 9/2011 | Sukhotnik et al. | |
| 8,877,232 B2 | 11/2014 | Barzilay | |
| 9,433,661 B2 * | 9/2016 | Guralnik | A61K 38/28 |
| 9,750,699 B2 | 9/2017 | Barzilay | |
| 2002/0064549 A1 | 5/2002 | Shehadeh | |
| 2002/0136809 A1 | 9/2002 | Shin | |
| 2003/0012819 A1 | 1/2003 | Ko | |
| 2003/0077297 A1 | 4/2003 | Chen | |
| 2003/0175403 A1 | 9/2003 | Gurin | |
| 2003/0190309 A1 | 10/2003 | Zink | |
| 2004/0037890 A1 | 2/2004 | Burger et al. | |
| 2004/0121002 A1 | 6/2004 | Lee | |
| 2006/0147494 A1 | 7/2006 | Barzilay | |
| 2007/0225211 A1 | 9/2007 | Sukhotnik et al. | |
| 2007/0248652 A1 | 10/2007 | Barzilay et al. | |
| 2010/0233274 A1 | 9/2010 | Shehadeh et al. | |
| 2015/0086622 A1 | 3/2015 | Hanien et al. | |
| 2015/0118280 A1 | 4/2015 | Barzilay | |
| 2015/0238573 A1 | 8/2015 | Barzilay | |
| 2017/0340567 A1 | 11/2017 | Barzilay | |

FOREIGN PATENT DOCUMENTS

| | | |
|---|---|---|
| EP | 0631731 A1 | 1/1995 |
| EP | 0495349 B1 | 8/1995 |
| EP | 0750854 A2 | 1/1997 |
| EP | 1214892 A1 | 6/2002 |
| EP | 1393636 A1 | 3/2004 |
| GB | 2345836 A | 7/2000 |
| JP | H10-155428 A | 6/1998 |
| JP | H11-009196 A | 1/1999 |
| JP | 2000-50793 A | 2/2000 |
| JP | 2000-050793 A | 2/2000 |
| JP | 2000-116320 A | 4/2000 |
| JP | 2002-209513 A | 7/2002 |
| JP | 2009-507067 A | 2/2009 |
| WO | WO 1988/001506 A1 | 3/1988 |
| WO | WO 1993/012772 A1 | 7/1993 |
| WO | WO 1998/044917 A1 | 10/1998 |
| WO | WO 1999/062558 A1 | 12/1999 |
| WO | WO 2002/058735 A1 | 8/2002 |
| WO | WO 2002/094224 A1 | 11/2002 |

(Continued)

OTHER PUBLICATIONS

PCT/US2017/024053, International Search Report and Written Opinion dated Jun. 28, 2017, 19 pages.
Dowling, Clare J., et al. "Severe gastroparesis diabeticorum in a young patient with insulin dependent diabetes." BMJ: British Medical Journal (1995); 310(6975): 308-311.
Shulman, Robert J., et al. "Evaluation of potential factors predicting attainment of full gavage feedings in preterm infants." Neonatology (2011); 99: 38-44.
European Patent Application No. EP 13777477.4, Extended European Search Report dated Aug. 25, 2015, 5 pages.
PCT/IL2013/050333, International Search Report and Written Opinion dated Jun. 25, 2013, 11 pages.
PCT/IL2013/050333, International Preliminary Report on Patentability dated Oct. 21, 2014, 8 pages.
Abell, Thomas L., et al. "Consensus recommendations for gastric emptying scintigraphy: a joint report of the American Neurogastroenterology and Motility Society and the Society of Nuclear Medicine." The American Journal of Gastroenterology (2008); 103.3: 753-763.

(Continued)

*Primary Examiner* — Robert A Wax
*Assistant Examiner* — Olga V Tcherkasskaya
(74) *Attorney, Agent, or Firm* — Cooley LLP (57) ABSTRACT

The present disclosure provides means and methods for promoting gastric emptying. In particular, the present disclosure provides the use of insulin or a composition comprising same for promoting gastric emptying and for treating gastric disorders, particularly disorders characterized by delayed gastric emptying. The insulin or composition comprising same are to be administered enterally.

23 Claims, 3 Drawing Sheets

(56) References Cited

FOREIGN PATENT DOCUMENTS

| WO | WO 2003/013538 A1 | 2/2003 |
|---|---|---|
| WO | WO 2003/030865 A1 | 4/2003 |
| WO | WO 2003/077661 A1 | 9/2003 |
| WO | WO 2004/003188 A2 | 1/2004 |
| WO | WO 2004/112494 A2 | 12/2004 |
| WO | WO 2005/115473 A2 | 12/2005 |
| WO | WO 2006/085100 A1 | 8/2006 |
| WO | WO 2009/086132 A2 | 7/2009 |
| WO | WO 2012/052060 A1 | 4/2012 |
| WO | WO 2012/150245 A1 | 11/2012 |
| WO | WO 2013/157003 A1 | 10/2013 |
| WO | WO 2017/165789 A1 | 9/2017 |

OTHER PUBLICATIONS

Bais, Janiek E., et al. "Impact of delayed gastric emptying on the outcome of antireflux surgery." Annals of Surgery (2001); 234.2: 139-146.
Bendayan et al., "Biochemical and morpho-cytochemical evidence for the intestinal absorption of insulin in control and diabetic rats. Comparison between the effectiveness of duodenal and colon mucosa." Diabetologia (1994); 37(2): 119-126.
Bielefeldt, Klaus. "Gastroparesis: concepts, controversies, and challenges." Scientifica (2012); vol. 2012, Article ID 424802, 19 pages.
Binder et al., "Insulin infusion with parenteral nutrition in extremely low birth weight infants with hyperglycemia." J Pediatr (1989); 114(2): 273-280.
Buts et al., "Oral insulin is biologically active on rat immature enterocytes." J Pediatr Gastroenterol Nutr (1997); 25(2): 230-232.
Cappello, Giorgio, et al. "Gastric emptying of a solid-liquid meal measured with 13C octanoic acid breath test and real-time ultrasonography: a comparative study." The American Journal of Gastroenterology (2000); 95.11: 3097-3100.
Corps and Brown, "Stimulation of intestinal epithelial cell proliferation in culture by growth factors in human and ruminant mammary secretions." J Endocrinol (1987); 113(2): 285-290.
Darwiche, Gassan, et al. "Correlation between simultaneous scintigraphic and ultrasonographic measurement of gastric emptying in patients with type 1 diabetes mellitus." Journal of Ultrasound in Medicine (2003); 22.5: 459-466.
Dollberg et al., "Birth weight standards in the live-born population in Israel." Isr Med Assoc J (2005); 7(5): 311-314.
ESPGHAN Committee on Nutrition et al., "Breast-feeding: A commentary by the ESPGHAN Committee on Nutrition." J Pediatr Gastroenterol Nutr (2009); 49(1): 112-125.
Finken et al., "Long-term height gain of prematurely born children with neonatal growth restraint: parallellism with the growth pattern of short children born small for gestational age." Pediatrics (2006); 118(2): 640-643.
Kinouchi et al., "Milk-borne insulin with trypsin inhibitor in milk induces pancreatic amylase development at the onset of weaning in rats." J Pediatr Gastroenterol Nutr (2000); 30(5): 515-521.
Kuczmarski et al., "2000 CDC Growth Charts for the United States: methods and development." Vital Health Stat (2002); 11 (246): 1-190, 203 pages.
Kuo, B., et al. "Comparison of gastric emptying of a nondigestible capsule to a radio-labelled meal in healthy and gastroparetic subjects." Alimentary Pharmacology & Therapeutics (2008); 27.2: 186-196.
Larkin, "Out with the jab, in with the painless pills." Lancet (1997); 349(9066): 1676, 1 page.
Marandi et al., "Insulin signal transduction in rat small intestine: role of MAP kinases in expression of mucosal hydrolases." Am J Physiol Gastrointest Liver Physiol (2001); 280(2): G229-G240.
Miyaji, H., et al. "The effect of Helicobacter pylori eradication therapy on gastric antral myoelectrical activity and gastric emptying in patients with non-ulcer dyspepsia." Alimentary Pharmacology and Therapeutics (1999); 13.10: 1303-1310.

Neu, Josef. "Gastrointestinal development and meeting the nutritional needs of premature infants." The American Journal of Clinical Nutrition (2007); 85.2: 629S-634S.
Ontsouka et al., "Effects of colostrum feeding and dexamethasone treatment on mRNA levels of insulin-like growth factors (IGF)-I and -II, IGF binding proteins-2 and -3, and on receptors for growth hormone, IGF-I, IGF-II, and insulin in the gastrointestinal tract of neonatal calves." Domestic Animal Endocrinology (2004); 26: 155-175.
Pillemer et al., "Insulin dependence of murine lymphoid T-cell leukemia." Int J Cancer (1992); 50(1): 80-85.
Read et al., "Changes in the growth-promoting activity of human milk during lactation." Pediatr Res (1984); 18(2): 133-139.
Schatz et al., Prevention of insulin-dependent diabetes mellitus: an overview of three trials. Cleve Clin J Med (1996); 63(5): 270-274.
Scientific Committee on Food; Report of the Scientific Committee on Food on the Revision of Essential Requirements of Infant Formulae and Follow-on Formulae, May 2003. Retrieved from: http://ec.europa.eu/food/fs/sc/scf/out199_en.pdf , 213 pages.
Shamir et al., "Atherosclerosis in apolipoprotein E-deficient mice is attenuated by entrally given insulin." Gastroenterology (2001); 120(5; supplement 1): A677; No. 3661.
Shamir et al., "Oral insulin supplementation attenuates atherosclerosis progression in apolipoprotein E-deficient mice." Arterioscler Thromb Vasc Biol (2003); 23(1): 104-110.
Shehadeh et al., "Gastrointestinal tract as a target organ for orally administered insulin." J Pediatr Gastroenterol Nutr (2006); 43(3): 276-281.
Shehadeh et al., "Importance of insulin content in infant diet: suggestion for a new infant formula." Acta Paediatr (2001); 90(1): 93-95.
Shehadeh et al., "Influence of oral insulin supplementation on carbohydrate, lipid and protein metabolism in weaned Balb/c mice." J Pediatr Endocrinol Metab (2003); 16(3): 431-437.
Shehadeh et al., "Insulin in human milk and the prevention of type 1 diabetes." Pediatr Diabetes (2001); 2(4): 175-177.
Shehadeh et al., Insulin in human milk: postpartum changes and effect of gestational age. Arch Dis Child Fetal Neonatal Ed (2003); 88(3): F214-F216.
Shulman, "Effect of enteral administration of insulin on intestinal development and feeding tolerance in preterm infants: a pilot study." Arch Dis Child Fetal Neonatal Ed (2002); 86(2): F131-133.
Shulman, "Oral insulin increases small intestinal mass and disaccharidase activity in the newborn miniature pig." Pediatr Res (1990); 28(2): 171-175.
Thabet et al., "Continuous insulin infusion in hyperglycaemic very-low-birth-weight infants receiving parenteral nutrition." Clin Nutr (2003); 22(6): 545-547.
Virtanen et al., "Infant feeding in Finnish children less than 7 yr of age with newly diagnosed IDDM. Childhood Diabetes in Finland Study Group." Diabetes Care (1991); 14(5): 415-417.
Wit et al., "Preterm growth restraint: a paradigm that unifies intrauterine growth retardation and preterm extrauterine growth retardation and has implications for the small-for-gestational-age indication in growth hormone therapy." Pediatrics (2006); 117(4): e793-795.
Wold, Agnes E., and Hanson, Lars Å. "Defense factors in human milk." Current Opinion in Gastroenterology (1994); 10.6: 652-658.
Zylberberg and Pepper, "Continuous insulin infusion: promoting growth in low birth weight infants." Source Kennedy HealthCare System, Washington Township, New Jersey, USA. Neonatal Network (2001); 20(1): 17-24.
"Breastfeeding and the use of Human Milk." American Academy of Pediatrics, Pediatrics (2012);129:e827-e841.
"Report of the Scientific Committee on Food on the Revision of Essential Requirements of Infant Formulae and Follow-on Formulae." European Commission, Health and Consumer Protection Directorate-General, Scientific Committee on Food (May 2003), 213 pages.
Adachi et al., "Preparation of a water-in-oil-in-water (W/O/W) Type Microcapsules by a Single-droplet-drying Method and Change in Encapsulation Efficiency of a Hydrophilic Substance during Storage." Bioscience, Biotechnology and Biochemistry (2003); 67(6): 1376-1381.

(56) References Cited

OTHER PUBLICATIONS

Agostoni, Carlo et al., "Breast-feeding: A Commentary by the ESPGHAN Committee on Nutrition." Journal of Pediatric Gastroenterology and Nutrition (2009); 49: 112-125.

Chantalau et al., "Insulin, insulin analogues and diabetic retinopathy." Archives of Physiology and Biochemistry (2008); 114(1): 54-62.

Extended European Search Report in EP Application No. 04744873.3 dated May 10, 2011, 5 pages.

Extended European Search Report in EP Application No. 05741069.8 dated Sep. 25, 2012, 6 pages.

Hou et al., "Applied studies of plant meridian system: I. The effect of agri-wave technology on yield and quality of tomato." Am J Chin Med (1999); 27(1): 1-10—abstract, Medline Accession No. 1999283208.

Hudayberdiyev et al., "Oral Multiple W/O/W Emulsion Formulation for Recombinant Human Insulin." Journal of Controlled Release (1997); 48: 346-347.

International Preliminary Report on Patentability for PCT/IL2004/000532 dated Jan. 3, 2006, 6 pages.

International Preliminary Report on Patentability for PCT/IL2005/000529 dated Nov. 29, 2006, 5 pages.

International Search Report for PCT/IL2004/000532 dated Oct. 3, 2005, 2 pages.

International Search Report for PCT/IL2005/000529 dated Jun. 15, 2006, 2 pages.

Raja, K.C.M., et al., "Material Characterization Studies of Maltodextrin Samples for the Use of Wall Material." Starch (1989); 41(8): 298-303.

Shamir et al., "Insulin in human milk and the use of hormones in infant formulas." The Importance of Immunonutrition. Nestlé Nutr Inst Workshop Ser. Nestec Ltd. (2013); vol. 77, pp. 57-64.

Whitmore, "Analysis of Insulin in Human Breast Milk in Mothers with Type 1 and Type 2 Diabetes Mellitus." International Journal of Endocrinology (2012); Article ID 296368, 9 pages.

Written Opinion for International Application No. PCT/IL2005/000529 dated Jun. 15, 2006, 4 pages.

Written Opinion for International Application No. PCT/IL2004/000532 dated Oct. 3, 2005, 5 pages.

\* cited by examiner

USE OF INSULIN FOR PROMOTING GASTRIC EMPTYING

CROSS REFERENCE TO RELATED APPLICATIONS

This application claims priority to U.S. Provisional Application No. 62/312,473, filed Mar. 24, 2016, which is hereby incorporated by reference in its entirety.

FIELD OF THE INVENTION

The present disclosure relates to methods and compositions for promoting gastric emptying, particularly to the use of insulin and/or a composition comprising same for treating delayed gastric emptying disorders in preterm babies and in other patient populations.

BACKGROUND OF THE INVENTION

Disorders of the stomach are very common and induce a significant amount of morbidity and suffering in the population. Data from hospitals indicate that more than 25% of the population suffers from some type of chronic stomach disorder including abdominal pain and indigestion. Many and various diseases can cause impairment of gastric function; the growing list ranges from functional changes after surgery to inherited disorders, neurologic diseases, connective tissue disorders, metabolic abnormalities, mental stress and infections. Premature infants and/or low birth weight infants have an immature gastrointestinal tract that can be associated with delayed gastric emptying.

Delayed gastric emptying is involved in many of the gastric diseases as a cause or as a result. Delayed gastric emptying may lead to negative nutritional and metabolic consequences. The impact of the often limited ability of patients to tolerate oral intake negatively affect the overall caloric intake, leading to deficiency and lack in essential nutrients.

Delayed gastric emptying affects tens of millions of patients who are diagnosed with various functional gastrointestinal disorders, including gastroesophageal reflux disease (GERD), non-ulcer dyspepsia (NUD) and gastroparesis (including diabetic gastroparesis, which affects half of all diabetes patients).

Many factors may cause delayed gastric emptying, not all of them are known. For example, the peptide hormone Cholecystokinin (CCK), which has most effect on gall bladder contractions, also decreases gastric emptying by contracting the Pylorus. The Pylorus is the lower section of the stomach that facilitates emptying the contents into the small intestine. Another example is the finding that patients with chronic *Helicobacter pylori* infection are likely to suffer from impaired gastric emptying.

GERD is typically caused by changes in the barrier between the stomach and the esophagus, causing expulsion of gastric reflux. It was shown to be associated with delayed gastric emptying in approximately 40% of the patients (Bais et al., Ann Surg. August 2001; 234(2): 139-146).

NUD is a general name for dyspepsia diseases that their cause is not known. Examples for known dyspepsia diseases are duodenal ulcer, stomach ulcer, oesophagitis (inflamed oesophagus), gastritis (inflamed stomach), etc. Delayed gastric emptying has been considered to play a role in NUD (Miyaji et al., Aliment Pharmacol Ther 1999; 13: 1303-1309).

Gastroparesis affects millions of individuals worldwide and most patients face a delay in diagnosis. In gastroparesis, the stomach motility is reduced and food remains stagnant in the stomach. The most common cause of gastroparesis is diabetes but it can also occur from a blockage at the distal end of stomach, a cancer or a stroke. Symptoms of gastroparesis includes abdominal pain, fullness, bloating, nausea, vomiting after eating food, loss of appetite and feeling of fullness after eating small amounts of food.

Gastroparesis is defined by the presence of dyspeptic symptoms and the documented delay in gastric emptying of ingested nutrients in the absence of gastric outlet obstruction (Klaus Bielefeldt, scientifca, Volume 2012, Article ID 424802, 19 pages).

Various methods are used for diagnosing delayed gastric emptying. For example, U.S. Pat. No. 6,548,043 discloses methods for measurement of gastric emptying. The method includes a test meal with $^{13}C$ tracer which is administered to a patient followed by measuring the breath sample for $^{13}CO_2$. The amount of $^{13}CO_2$ over time determines the gastric emptying activity. In neonates, aspiration of gastric residuals and measurement of the aspirated volume can be an indicator of gastric emptying.

There is a recognized need for additional therapeutic means and compositions for treating gastric disorders, particularly delayed gastric emptying disorders.

SUMMARY OF THE INVENTION

The present disclosure provides methods and compositions for treating gastric disorders. The present disclosure further provides, according to some embodiments the use of insulin in treating gastric diseases and/or disorders characterized by delayed gastric emptying.

The present disclosure is based in part on the unexpected discovery that oral insulin treatment improves the rate of gastric emptying. Insulin enterally administered to preterm infants decreased the amounts of their gastric residuals, indicating an improved gastric emptying efficiency. Strikingly, the enteral administration of insulin to preterm infants resulted in a statistically significant reduction in gastric residuals relative to placebo control treated preterm infants. The enterally administered insulin according to the teaching of the present disclosure is not expected to reach the blood circulation. Enteral administration of insulin would not be expected to have either a direct or an indirect effect on gastric emptying; therefore, the fact that a statistically significant reduction in gastric residuals achieved in preterm infants was particularly surprising. Radioligand binding experiments have documented the presence of insulin receptors in mammal enterocytes; therefore, without wishing to be bound by any specific theory or mechanism of action, the effect of insulin on gastric emptying may be attributable in whole or in part to an indirect signaling effect.

According to one aspect, the present disclosure provides a method for promoting gastric emptying in a subject in need thereof, comprising the step of enterally administering an effective amount of insulin or a composition comprising same to the subject, thereby promoting the gastric emptying.

In some embodiments, the subject suffers from a gastric disorder.

In some embodiments, the gastric disorder is characterized by delayed gastric emptying.

In some embodiments, the gastric disorder is selected from the group consisting of: gastroesophageal reflux disease (GERD), non-ulcer dyspepsia (NUD), and gastroparesis. In further embodiments, the gastroparesis is a diabetic gastroparesis.

In some embodiments, the subject does not suffer from a gastric disorder. In some embodiments, the delayed gastric emptying is caused by a factor selected from the group consisting of: surgery; consumption of certain medicines; virus infection; diseases affecting the nerves, muscles, hormones and/or metabolism of the subject, including diabetes; chronic diseases including anorexia or bulimia; cancer treatment; tobacco consumption; and alcohol consumption.

In some embodiments the subject is a human subject. In other embodiments, the subject is a non-human mammal.

According to certain embodiments, the human subject is an adult. According to other embodiments, the human subject is at the age of 2-18 years. According to additional embodiments, the human subject is at the age of above 18. According to yet additional embodiments, the human subject is at the age of 1 month to 24 months.

According to further embodiments, the human subject is a neonate. In some embodiments, the human subject is a preterm infant. In some embodiments, the human subject is a low birth weight human. In some embodiments, "preterm infant" refers to a human infant born at a gestational age of 24 to 32 weeks. In some embodiments, the subject is an infant born at a gestational age of 26 to 32 weeks. In some embodiments, the subject is an infant born at a gestational age of 24 to 28 weeks. In some embodiments, the subject is an infant born at a gestational age of 26 to 28 weeks. In other embodiments, the subject is an infant born at a gestational age of 29 to 32 weeks. In some embodiments, the present disclosure provides methods for promoting gastric emptying in human infant subjects, wherein the infant is enterally administered insulin for up to 28 days, or until the infant is discharged from the hospital. In some embodiments, the enteral administration of insulin to the human infant subject provides a statistically significant therapeutic effect in reducing gastric residuals in the subject. In some embodiments, the therapeutic effect is measured by the time (e.g., the number of days) of treatment until which gastric residuals over 2 ml/measurement no longer occur in the subject. In further embodiments, the therapeutic effect is measured by the time of treatment until which no gastric residuals are emitted in the subject. In other embodiments, the therapeutic effect is measured by the number of days to reach gastric residuals of <2 ml/kg body weight. In further embodiments, the therapeutic effect is measured by the number of days to reach gastric residuals of 0 mg/kg body weight. Thus, in some embodiments, the present disclosure provides methods for promoting gastric emptying in a subject wherein the method provides statistically significant improvement in the number of days to end gastric residuals over 2 m/measurement; the number of days to end emission of gastric residuals; the number of days to reach gastric residuals of <2 ml/kg body weight; the number of days to reach gastric residuals of 0 mg/kg body weight; or a combination thereof.

In some embodiments, the insulin has the amino acid sequence of human insulin or functional equivalent thereof. In some embodiments, the insulin is mammalian insulin selected from the group consisting of human insulin and bovine insulin. In other embodiments, the insulin is recombinant insulin or synthetic insulin. In yet other embodiments, the insulin is synthetic insulin.

In some embodiments, the insulin is encapsulated in an encapsulating material. In certain embodiments, the encapsulating materials are selected from the group consisting of polysaccharides, milk powder, whey proteins, lipids, gum Arabic and microcrystalline cellulose. Other encapsulation materials well known in the art are also encompassed within the scope of the present disclosure.

The insulin can be administered per se, as an encapsulated form and/or as part of a composition. In one embodiment, insulin is microencapsulated within a matrix of maltodextrin (MD) to form an insulin supplement, suitable for use in pharmaceutical compositions or nutritional formulae. According to other embodiments, the matrix further comprises anti oxidant, typically vitamin C. This matrix provides the encapsulated insulin with a long term stability and resistance to exposure to high temperatures (above 42° C.) in terms of preserved activity.

According to the teachings of the present disclosure, insulin can be administered directly, within a composition and/or with another drug. Any method for enteral administration known in the art can be used according to the teachings of the present disclosure. For example, the enteral administration is selected from the group consisting of oral, sublingual, rectal, or via a feeding tube. In some embodiments, the insulin is administered orally. According to certain embodiments, the insulin is administered in a pharmaceutical composition; the pharmaceutical composition further comprises a pharmaceutically acceptable diluent, excipient or carrier. According to other embodiments, the insulin is administered in a nutritional composition. The pharmaceutical or nutritional compositions of the present disclosure can be administered by normal feeding or sublingually, or, alternatively, particularly when normal feeding is not possible, via a nasogastric tube, gastrostomy or jejunostomy.

According to certain embodiments, the insulin or the composition comprising same is administered orally. According to additional embodiments the insulin or the composition comprising same is administered by a nasogastric tube.

In some embodiments, the oral administration is affected by an oral dosage unit. In some embodiments, the oral dosage unit is solid. In certain embodiments, the oral dosage unit is selected from the group consisting of a powder, a pill, a dragee, a tablet and a capsule. According to certain embodiments, the tablet is in a form of chewable and/or fast dissolve tablet. According to other embodiments, the insulin or encapsulated insulin is embedded within a gel. According to some exemplary embodiments, the gel is coated to form a dragee or a capsule.

In some embodiments, the oral dosage unit comprises from about 1 mU to about 10,000 U of insulin. In other embodiments, the oral dosage unit comprises insulin in a concentration from about 0.02 U/gr to about 50 U/gr. In some embodiments, the oral dosage unit comprises insulin in a concentration from about 0.04 U/gr to about 20 U/gr. In some embodiments, the oral dosage unit comprises insulin in a concentration of about 0.01 U/gr, about 0.02 U/gr, about 0.03 U/gr, about 0.04 U/gr, about 0.05 U/gr, about 0.06 U/gr, about 0.07 U/gr, about 0.08 U/gr, about 0.09 U/gr, about 0.1 U/gr, about 0.2 U/gr, about 0.3 U/gr, about 0.4 U/gr, or about 0.5 U/gr.

According to additional embodiments, the composition comprising the insulin or encapsulated insulin is in a form of a powder. According to certain exemplary embodiments, the powder is ready for reconstitution with a liquid. Any liquid suitable for enteral consumption can be used according to the teachings of the present disclosure. According to some embodiments, the liquid is water or normal saline. According to other embodiments, the liquid is a ready to use nutritional liquid formula. According to some embodiments, the nutritional liquid is formulated for adults. According to other embodiments, the nutritional liquid is formulated for children, infants or neonates. Accordingly, in some embodiments, insulin is administered directly, within a composition and/or within an infant formula. In further embodiments, the insulin or a composition comprising the insulin is mixed with infant formula to form an insulin-enriched formula. Any infant formula as is known in the art can be used as a basal formula for producing the insulin-enriched formula. Typically, the infant formula is in a form of dry powder that may be reconstituted to form a liquid formula prior to use. In some embodiments, the dry powder is reconstituted with water or normal saline and can be administered with or without infant formula.

In some embodiments, the insulin is administered to the subject in a formulation comprising an insulin concentration from about 100 µU/mL to about 4000 µU/mL. In some embodiments, the insulin is administered to the subject in a formulation comprising an insulin concentration from about 200 µU/mL to about 3000 µU/mL. In some embodiments, the insulin is administered to the subject in a formulation comprising an insulin concentration from about 400 µU/mL to about 2000 µU/mL. In some embodiments, the insulin is administered to the subject in a formulation comprising an insulin concentration of about 400 µU/mL. In other embodiments, the insulin is administered to the subject in a formulation comprising an insulin concentration of about 2000 µU/mL.

In some embodiments, the insulin is administered to the subject in an infant formula. In some embodiments, the total amount of insulin administered to the subject is from about 0.5 mU/kg/day to about 1 U/kg/day. In some embodiments, the total amount of insulin administered to the subject is from about 0.001 U/kg/day to about 0.5 U/kg/day. In some embodiments, the total amount of insulin administered to the subject is from about 0.005 U/kg/day to about 0.1 U/kg/day. In some embodiments, the total amount of insulin administered to the subject is from about 0.01 U/kg/day to about 0.05 U/kg/day. In some embodiments, the total amount of insulin to be administered to the subject is from about 0.05 U/kg/day to about 0.1 U/kg/day. In some embodiments, the total amount of insulin to be administered to the subject is from about 0.1 U/kg/day to about 0.5 U/kg/day.

In some embodiments, the insulin is administered in an amount ranging from about 1 mU/Kg body weight/day to about 100 U/Kg body weight/day. In other embodiments, the insulin is administered in an amount ranging from about 50 mU/Kg body weight/day to about 10 U/Kg body weight/day. In certain embodiments, the insulin is administered in an amount ranging from about 0.1 U/Kg body weight/day to about 2 U/Kg body weight/day. In some embodiments, the insulin is administered in an amount of about 1 U/kg/day. In some embodiments, the insulin is administered in an amount of about 2 U/kg/day. In some embodiments, the insulin is administered in an amount of about 4 U/kg/day. In some embodiments, the insulin is administered in an amount of about 8 U/kg/day.

In some embodiments, the present disclosure provides methods for promoting gastric emptying in a subject, wherein the method provides a statistically significant therapeutic effect in promoting gastric emptying in the subject, and wherein the method comprises enterally administering insulin to the subject in an amount of about 400 µU/mL or about 2000 µU/mL. In some embodiments, the present disclosure provides methods for reducing gastric residuals in a subject, wherein the method provides a statistically significant therapeutic effect in reducing gastric residuals in the subject, and wherein the method comprises enterally administering insulin to the subject in an amount of about 400 µU/mL or about 2000 µU/mL.

Promoting gastric emptying can be useful also when other drugs are consumed. An efficient emptying of the stomach allows the arrival of the drug in its intact form to the intestine where it is absorbed. Thus, according to some embodiments, the method of the present disclosure is used for treating a subject that needs an improved gastric emptying rate, particularly a subject consuming at least additional drug. In some embodiments, the subject is not suffering from gastric disorder. In some embodiments, the insulin is enterally administered prior to, concomitant with or following administration of additional pharmacological agent. In certain embodiments, the additional pharmacological agent is selected from the group consisting of cisapride ((±)cis-4-amino-5-chloro-N-(1-[3-(4-fluorophenoxy)propyl]-3-methoxypiperidin-4-yl)-2-methoxybenzamide), domperidone (4-(5-chloro-2-oxo-1-benzimidazolinyl)-1-[3-(2-oxobenzimidazolinyl)propyl]piperidine), erythromycin, bile acid, lipase inhibitor, and metoclopramide (4-amino-5-chloro-N-(2-(diethylamino)ethyl)-2-methoxybenzamide).

In some embodiments, the insulin is orally administered prior to, concomitant with or following administration of probiotics and/or prebiotics.

Gastric emptying parameters can be determined by variety of methods and techniques. In some embodiments, promoting gastric emptying is increasing gastric emptying by at least 5%, 10%, 20%, 30%, 40%, 50%, 60%, 70%, 80%, 90% or 95% compared to gastric emptying in the subject before treatment with insulin or gastric emptying in a corresponding subject not treated with insulin. As used herein, the term "corresponding subject" refers to a subject having equivalent characteristic in terms of age, gender, presence of a disease, type of the disease and severity of the disease.

According to another aspect, the present disclosure provides insulin and/or a composition comprising same for use in promoting gastric emptying, wherein the insulin and/or composition comprising same is to be administered enterally.

According to an additional aspect, the present disclosure provides a pharmaceutical composition comprising insulin and at least one pharmaceutically acceptable carrier, excipient or diluent for use in the treatment of gastric disorder, wherein the pharmaceutical composition is formulated for enteral administration.

According to yet a further aspect, the present disclosure provides a nutritional composition comprising insulin for use in promoting gastric emptying.

According to certain exemplary embodiments, the gastric disorder is characterized by delayed gastric emptying.

In yet another aspect, the present disclosure provides the use of insulin or equivalent thereof in the manufacture of a medicament for the treatment of gastric disorder.

In an additional aspect, the present disclosure provides a kit for use in promoting gastric emptying, the kit comprising:
  (i) pharmaceutical composition comprising insulin, or equivalent thereof, and a pharmaceutically acceptable carrier, excipient or diluent; and
  (ii) written instruction for use of said pharmaceutical composition.

In yet an additional aspect, the present disclosure provides a kit for use in promoting gastric emptying, the kit comprising:

(i) nutritional composition comprising insulin, or equivalent thereof, and a carrier, excipient or diluents suitable for oral use; and (ii) written instruction for use of said composition.

The gastric disorder, the insulin, the dosage unit and route of administration are as described hereinabove.

In some embodiments, the present disclosure provides methods for making, preparing, mixing, or compounding an infant feed formulation provided herein, wherein the formulation comprises an insulin composition provided herein and an infant's nutrition composition. Infant nutrition is selected from, for example formula, donor breast milk (DBM), or own mother's breast milk (OMM). In some embodiments, the insulin is in powder form. In some embodiments, the insulin powder is reconstituted in milk or infant formula. In other embodiments, the insulin is reconstituted in saline (e.g., normal saline (0.9% NaCl) or half normal saline (0.45% NaCl)) prior to mixing with the formula, DBM, or OMM. In some embodiments, the insulin composition is provided in a concentration from about 0.05 U/g to about 0.1 U/g. In some embodiments, the insulin composition is provided in a concentration of 0.2 U/g. In other embodiments, the insulin composition is provided in a concentration of 0.04 U/g. An appropriate amount of powder is added to the infant nutrition or saline to achieve the desired volume of infant feed formulation. For example, in some embodiments, if the infant requires 100 mL of nutrition, then 1 g of insulin composition in powder form at a concentration of 0.04 U/g may be added to 100 mL of infant nutrition to achieve an infant feed formulation comprising insulin at a concentration of 400 µU/mL. In other embodiments, if the infant requires 100 mL of nutrition, then 1 g of insulin composition in powder form at a concentration of 0.2 U/g may be added to 100 mL of infant nutrition to achieve an infant feed formulation comprising insulin at a concentration of 2000 µU/mL.

It is to be understood explicitly that the scope of the present disclosure encompasses homologs, analogs, variants and derivatives, including shorter and longer polypeptides, proteins, as well as polypeptide and protein analogs with one or more amino acid substitution, as well as amino acid derivatives, non-natural and synthetic amino acids as are known in the art, with the stipulation that these variants and modifications must preserve the therapeutically effect of insulin in treating gastric disorders. Specifically, any active fragments of the active polypeptide or protein as well as extensions, conjugates and mixtures are disclosed according to the principles of the present disclosure.

Other objects, features and advantages of the present disclosure will become clear from the following description and drawings.

DETAILED DESCRIPTION OF THE INVENTION

The present disclosure provides methods and compositions for promoting gastric emptying, particularly for treating preterm or low birth weight infants or for treating gastric disorders characterized by delayed gastric emptying. The present disclosure further provides the use of insulin in promoting the delayed gastric emptying and/or treating its symptoms. The disclosure is based on the surprising discovery that insulin treatment, orally administered to preterm infants without affecting the blood glucose or insulin levels, decreased the gastric residual occurrence. The decrease in gastric residuals was statistically significant relative to placebo control treated preterm infants.

Without wishing to be bound by theory or mechanism, the insulin or composition comprising same administered to the digestive system act locally on gastrointestinal receptors, and exerts it effect locally in the gastrointestinal tract. The insulin, equivalent thereof and/or compositions comprising same are administered enterally, typically orally, and are not expected to reach the bloodstream and affect the sugar level.

According to one aspect, the present disclosure provides a method for improving gastric emptying in a subject in need thereof, comprising the step of administering enterally insulin to said subject, thereby improving said gastric emptying.

The term "delayed gastric emptying" refers to disorder or condition that slows or stops the movement of food from the stomach to the small intestine. "Gastric residual" and the like refers to any leftover nutrition in the stomach that was not digested or absorbed by the body.

The terms "promoting gastric emptying" or "improving gastric emptying" are used herein interchangeably and refer to increasing the flow or passage of food from the stomach to the small intestine. The increase of food passage is intended to prevent or decrease the deleterious effects of food that stuck in the stomach. Non-limiting example of a possible deleterious effect is increased reflux. In some embodiments, "reducing gastric residuals" and the like refers to a reduction in the presence of gastric residuals, which one measure of promoting gastric emptying.

The term "insulin" is used in the broadest sense and includes human insulin peptide as well as other non-human insulin peptide, homologs, analogs, variants and derivative of the peptide, with the stipulation that they possess the same activity as the naturally occurring insulin peptide. As used herein, the terms "U" (units) or "IU" (International Unit) are used herein interchangeably and refer to the biological equivalent of about 34.7 µg pure crystalline insulin (exactly 1/28.8 mg).

The term "treating" as used herein, includes, but is not limited to any one or more of the following: abrogating, ameliorating, inhibiting, attenuating, blocking, suppressing, reducing, delaying, halting, alleviating or preventing the symptoms associated with the gastric disorder, in particular delayed gastric emptying symptoms.

As used herein the phrase "subject in need thereof" refers to a human or non human mammal. The human or non human mammal can be of any age (e.g., infant such as term or preterm infant, adult or old) or sex, which can benefit from improved gastric emptying. According to certain exemplary embodiments, the human subject is a preterm infant and/or a low birth weight infant. In some embodiments, a preterm infant is an infant born at a gestational age of 24 to 33 weeks. In some embodiments, a preterm infant is an infant born at a gestational age of 26 to 33 weeks. In some embodiments, the subject is an infant born at a gestational age of 24 to 28 weeks. In some embodiments, the subject is an infant born at a gestational age of 26 to 28 weeks. In other embodiments, the subject is an infant born at a gestational age of 29 to 32 weeks. In some embodiments, a low birth weight infant is an infant weighing about 1650 g at birth or less. In some embodiments, a low birth weight infant is an infant weighing from about 500 g to about 1650 g at birth. In other embodiments, the human subject is selected from the group consisting of children at age of 2-9, young adolescent at age of 9-13, adolescent at age of 13-18 and adults at any age above 18. Examples of non-human mammals include domestic animals such as cats, dogs, cattle, sheep, pigs, goats and equines.

As used herein a "pharmaceutical composition" refers to a preparation of insulin with other components such as pharmaceutically acceptable carriers, diluents and excipients. The purpose of a pharmaceutical composition is to facilitate administration of a compound to a subject.

The terms "nutritional formula" or "nutritional composition" are used herein interchangeably and refer to nutritional liquids and/or nutritional solids that comprise insulin according to the disclosure and at least one of protein, fat, and/or carbohydrate, suitable for oral administration to a human or non-human mammal. The nutritional composition may further comprise vitamins, minerals, and other ingredients and represent a sole, primary, or supplemental source of nutrition.

As used herein, the term "excipient" refers to an inert substance added to a pharmaceutical composition to further facilitate administration of the insulin. Examples, without limitation, of excipients include calcium carbonate, calcium phosphate, various sugars and types of starch, cellulose derivatives, gelatin, vegetable oils, and polyethylene glycols.

The term "pharmaceutically acceptable" means approved by a regulatory agency of the Federal or a state government or listed in the U.S. Pharmacopeia or other generally recognized pharmacopeia for use in animals, and more particularly in humans.

As used herein, the phrase "pharmaceutically acceptable carrier" refers to a carrier, an excipient or a diluent that does not cause significant irritation to an organism and does not abrogate the biological activity and properties of the administered compound.

As used herein, the term "carrier" refers to any substance suitable as a vehicle for delivering of the insulin of the present disclosure to a suitable biological site or tissue. As such, carriers can act as a pharmaceutically acceptable excipient of the pharmaceutical composition of the present disclosure. Carriers of the present disclosure include: (1) excipients that transport, but do not specifically target a molecule to a cell (non-targeting carriers); and (2) excipients that deliver a molecule to a specific site in a subject or a specific cell (targeting carriers). Examples of non-targeting carriers include, but are not limited to water, phosphate buffered saline, Ringer's solution, dextrose solution, serum-containing solutions, Hank's solution, other aqueous physiologically balanced solutions, oils, esters and glycols. Aqueous carriers can contain suitable auxiliary substances required to approximate the physiological conditions of the recipient, for example, by enhancing chemical stability and isotonicity.

Furthermore, the pharmaceutical composition according to the disclosure may comprise one or more stabilizers such as, for example, carbohydrates including sorbitol, mannitol, starch, sucrose, dextrin and glucose, proteins such as albumin or casein, and buffers like alkaline phosphates. Pharmaceutical compositions of the present disclosure may be sterilized by conventional methods.

The pharmaceutical compositions of the present disclosure may be manufactured by processes well known in the art, e.g. by means of conventional mixing, dissolving, granulating, dragee-making, levigating, emulsifying, encapsulating, entrapping, or lyophilizing processes.

For oral administration, the pharmaceutical composition can be formulated readily by combining the active compounds with pharmaceutically acceptable carriers well known in the art. Such carriers enable the pharmaceutically composition to be formulated as tablets, pills, dragees, capsules, liquids, gels, syrups, slurries, suspensions, and the like.

Pharmaceutical compositions which can be used orally include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers.

The dosage of a composition to be administered will depend on many factors including the subject being treated, the stage of cancer, the route of administration, and the judgment of the prescribing physician.

Gastric Emptying Assessment

A variety of tests have been developed to measure gastric emptying. Since its initial description more than 40 years ago, scintigraphic assessment has been widely accepted and has become the "gold standard" for the diagnosis of gastroparesis (Abell T L., The American Journal of Gastroenterology, vol. 103, no. 3, pp. 753-763, 2008). Early on, investigators recognized the importance of volume, caloric content, nutrient composition, and consistency in determining the rate of gastric emptying. To minimize variability and allow comparisons, the test should use a predefined volume and caloric load and should be carried out over 4 h. Using such approaches, repeat testing shows an acceptable intraindividual reproducibility despite significant variability between persons.

In addition, assessment of gastric emptying by measuring gastric residuals is considered standard of care for infants in the neonatal intensive care unit. Measurement of gastric residuals is routinely conducted by aspiration.

Additional tests for assessing gastric emptying have been developed. Ultrasound can be used to monitor antral contractions and determine the volume changes after a mixed meal. The results correlate reasonably well with scintigraphic determination of gastric emptying (Darwiche, G. Journal of Ultrasound in Medicine, vol. 22, no. 5, pp. 459-466, 2003). However, interference due to intraluminal air and the difficulty in monitoring obese patients limits the clinical utility of this approach. Magnetic resonance imaging can similarly address contractions and volume changes, thus allowing determining accommodation and emptying after a test meal. Cost and complexity of data analysis argue against a widespread use of this approach.

Using stable nonradioactive carbon isotopes (e.g., labeled fatty acids) in a test meal, one can determine time-dependent changes in these isotopes in the exhaled air, as the ingested material is absorbed and metabolized once it exited the stomach. Such breath tests have an acceptable intra-individual variability of around 15% and correlate reasonably well with scintigraphic assessments of gastric emptying (Delbende.B European Journal of Gastroenterology and Hepatology, vol. 12, no. 1, pp. 85-91, 2000). In 2005, the U.S. Food and Drug Administration approved the Gastric Emptying Breath Test (GEBT). The GEBT, conducted over a four-hour period after an overnight fast, is designed to show how fast the stomach empties solids by measuring carbon dioxide in a patient's breath. Patients have baseline breath tests conducted at the beginning of the test. They then eat a special test meal that includes a scrambled egg-mix and Spirulina platensis, a type of protein that has been enriched with carbon-13, which can be measured in breath samples. By adding carbon-13 to the test meal, the GEBT can determine how fast the stomach empties the meal by measuring the ratio of carbon-13 to carbon-12 collected in breath samples at multiple time points after the meal is consumed compared to baseline.

A wireless capsule has been introduced as an alternative technique for monitoring gastric emptying. Being a large particle, it typically will not exit the stomach with the meal, but will be expelled during the repeated high amplitude contractions of the phase III activity of the migrating motor complex, which resumes after completion of gastric emptying. The entry into the duodenum is indicated by the sudden jump in pH and correlates reasonably well with scintigraphic findings (Kuo, B Alimentary Pharmacology & Therapeutics, vol. 27, no. 2, pp. 186-196, 2008).

Recordings of intraluminal pressure or gastric electrical activity have been proposed as diagnostic tests in patients with dyspeptic symptoms. While these tests often show abnormalities in patients with gastroparesis, they can at best correlate with but do not assess transit. As prolonged retention of ingested material defines the currently accepted endophenotype, assessment of contractile or electrical activity may provide additional mechanistic insights, but does not truly aide in the diagnosis of gastroparesis.

Therapeutic Use

The present disclosure provides a method of promoting gastric emptying comprising administering insulin to a subject in need thereof.

According to an additional aspect, the present disclosure provides a method for promoting gastric emptying in a subject in need thereof, comprising the step of administering a composition comprising an effective amount of insulin to said subject, thereby promoting said gastric emptying.

According to another aspect, the present disclosure provides a pharmaceutical composition formulated for enteral administration, for use in promoting gastric emptying, comprising insulin and at least one pharmaceutically acceptable carrier, excipient or diluent.

The term "an effective amount" of the compound is that amount of the compound which is sufficient to provide a beneficial effect to the subject to which the compound is administered. An effective amount of the compound may vary according to factors such as the type of disease or disorder, disease state, age, sex, and weight of the individual.

According to an additional aspect, the present disclosure provides a nutritional composition formulated for use in improving gastric emptying, comprising insulin and at least one carrier, excipient or diluents suitable for oral use.

According to yet additional aspect, the present disclosure discloses the use of an effective amount of insulin for the preparation of a composition for promoting gastric emptying, wherein the composition is formulated for enteral administration. In some embodiments, the subject is a preterm infant and/or a low birth weight infant. In some embodiments, the subject suffers from a gastric disorder that is characterized by delayed gastric emptying. In certain embodiments, the gastric disorder is selected from the group consisting of: gastroesophageal reflux disease (GERD), non-ulcer dyspepsia (NUD), and gastroparesis. In certain embodiments, the gastroparesis is a diabetic gastroparesis.

Patients with GERD may have either normal or abnormal gastric emptying. However, gastric motor derangement, when present, appears to be associated with the development of esophagitis. Delayed gastric emptying indeed will increase the volume of gastric contents available for reflux and, in conjunction with a delayed esophageal clearance, will strongly prolong the esophageal exposure to acid, thus resulting in development of mucosal damage. A treatment with insulin according to the disclosure may accelerate gastric emptying and reduce esophageal exposure to acid. According to some embodiments, there is provided a use of insulin or pharmaceutical composition comprising insulin for improving delayed gastric emptying in GERD patients.

Non-ulcer dyspepsia is diagnosed in patients that suffer from variety of gastro-related symptoms such as abdominal pain, bloating, nausea, and vomiting and no evidence of an organic disease that is likely to explain the symptoms is found. Many patients with non-ulcer dyspepsia have multiple somatic complaints, as well as symptoms of anxiety and depression. High percent of patients with non-ulcer dyspepsia exhibit motility dysfunction which may result, inter alia, in delayed gastric emptying. According to some embodiment, there is provided the use of insulin or a pharmaceutical composition comprising insulin for improving delayed gastric emptying in non-ulcer dyspepsia patients.

Delayed gastric emptying can be a symptom or result of variety of external factors that are not related to a gastric disease. In some embodiments, the delayed gastric emptying is caused by a factor selected from the group consisting of: surgery (for example, surgery on the stomach or vagus nerve); consumption of certain medicines; virus infection; diseases affecting nerves, muscles, hormones and/or metabolism including diabetes; chronic diseases including anorexia or bulimia; cancer treatment; tobacco consumption; and alcohol consumption. Non-limiting examples for medications that may cause delayed gastric emptying include: gastrointestinal agents, anticholinergic medications (e.g., Diphenhydramine (Benadryl), Opioid Analgesics, Tricyclic Antidepressants, and Oxybutynin), and diabetes medications (e.g., Exenatide, Liraglutide, and Pramlintide). Non-limiting examples of diseases affecting nerves, muscles, hormones, and/or (including, for example, diabetes, nervous system diseases, smooth muscle disorders)

According to some embodiments, the insulin or pharmaceutical composition comprising same is administered at least once a month. According to additional embodiments, insulin the pharmaceutical composition comprising same is administered at least twice a month. According to further embodiments, the insulin or pharmaceutical composition comprising same is administered at least once a week. According to yet further embodiments, the insulin or pharmaceutical composition comprising same is administered at least twice a week. According to still further embodiments, the insulin or pharmaceutical composition comprising same is administered once a day for at least one week. According to further embodiments, the insulin or pharmaceutical composition comprising same is administered at least once a day for at least one week or until the subject is cured.

According to some embodiments, the insulin or the composition comprising same is administered once a day for at least 2, 3, 4, 5, 6, 8, 10, 12, or at least 14 consecutive days once a month. Alternatively, insulin or the composition comprising same is administered once a day for at least 2, 3, 4, 5, 6, or 12 days twice a month, or further alternatively the insulin or the composition comprising same is administered every day or twice a week until the patient is cured.

The insulin or the pharmaceutical or nutritional composition comprising same may be administered regularly for prolonged periods of time according to the clinician's instructions.

In some cases it may be advantageous to administer a large loading dose followed by periodic (e.g., weekly) maintenance doses over the treatment period. The insulin can also be delivered by slow-release delivery compositions and/or systems and other known delivery systems for continuous delivery.

Typically, the effective dose is determined by the activity and efficacy of the compound and the condition of the subject as well as the body weight or surface area of the subject to be treated. The dose and the dosing regimen are also determined by the existence, nature, and extent of any adverse side effects that accompany the administration of the compounds in a particular subject.

The insulin contained composition of the disclosure may be orally administered in a single dosage unit. In some embodiments, the oral dosage unit comprises from about 1 mU to about 10,000 U of insulin. In other embodiments, the oral dosage unit comprises insulin in a concentration from about 0.02 U/gr to about 50 U/gr. In some embodiments, the oral dosage unit comprises insulin in a concentration from about 0.04 U/gr to about 20 U/gr. In some embodiments, the insulin is administered to the subject in an amount of from about 1 µU/mL to about 1 U/mL. In further embodiments, the insulin is administered to the subject in a composition comprising insulin at a concentration from about 10 µU/mL to about 0.1 U/mL. In further embodiments, the concentration of insulin is from about 100 µU/mL to about 0.01 U/mL. In further embodiments, the concentration of insulin is from about 400 µU/mL to about 0.002 U/mL. In some embodiments, the concentration of insulin is about 100 µU/mL. In some embodiments, the concentration of insulin is about 200 µU/mL. In some embodiments, the concentration of insulin is about 300 µU/mL. In some embodiments, the concentration of insulin is about 400 µU/mL. In some embodiments, the concentration of insulin is about 500 µU/mL. In some embodiments, the concentration of insulin is about 600 µU/mL. In some embodiments, the concentration of insulin is about 700 µU/mL. In some embodiments, the concentration of insulin is about 800 µU/mL. In some embodiments, the concentration of insulin is about 900 µU/mL. In some embodiments, the concentration of insulin is about 1000 µU/mL. In some embodiments, the concentration of insulin is about 1200 µU/mL. In some embodiments, the concentration of insulin is about 1400 µU/mL. In some embodiments, the concentration of insulin is about 1600 µU/mL. In some embodiments, the concentration of insulin is about 1800 µU/mL. In some embodiments, the concentration of insulin is about 2000 µU/mL.

In some embodiments, the insulin is administered to the subject in an infant formula or in milk. In some embodiments, the amount of insulin administered to the subject per day is dependent on the nutritional needs of the infant, which may be influenced by the infant's age, weight, and clinical condition. Thus, in some embodiments, the amount of insulin administered to the subject per day depends on the total amount of feed provided to the infant, wherein the feed contains a particular concentration of insulin. In some embodiments, the total amount of insulin administered to the subject is from about 0.5 mU/kg/day to about 1 U/kg/day. In some embodiments, the total amount of insulin administered to the subject is from about 0.001 U/kg/day to about 0.5 U/kg/day. In some embodiments, the total amount of insulin administered to the subject is from about 0.005 U/kg/day to about 0.1 U/kg/day. In some embodiments, the total amount of insulin administered to the subject is from about 0.01 U/kg/day to about 0.05 U/kg/day. In some embodiments, the total amount of insulin administered to the subject is about 0.01 U/kg/day, about 0.02 U/kg/day, about 0.03 U/kg/day, about 0.04 U/kg/day, about 0.05 U/kg/day, about 0.06 U/kg/day, about 0.07 U/kg/day, about 0.08 U/kg/day, about 0.09 U/kg/day, about 0.1 U/kg/day, about 0.2 U/kg/day, about 0.3 U/kg/day, about 0.4 U/kg/day, about 0.5 U/kg/day, about 0.6 U/kg/day, about 0.7 U/kg/day, about 0.8 U/kg/day, about 0.9 U/kg/day, or about 1.0 U/kg/day.

In some embodiments, the insulin is administered in an amount ranging from about 1 mU/Kg body weight/day to about 100 U/Kg body weight/day. In other embodiments, the insulin is administered in an amount ranging from about 50 mU/Kg body weight/day to about 10 U/Kg body weight/day. In certain embodiments, the insulin is administered in an amount ranging from about 0.1 U/Kg body weight/day to about 2 U/Kg body weight/day. In some embodiments, the insulin is administered in an amount of about 0.1 U/kg/day. In some embodiments, the insulin is administered in an amount of about 0.5 U/kg/day. In some embodiments, the insulin is administered in an amount of about 1 U/kg/day. In some embodiments, the insulin is administered in an amount of about 2 U/kg/day. In some embodiments, the insulin is administered in an amount of about 4 U/kg/day. In some embodiments, the insulin is administered in an amount of about 6 U/kg/day. In some embodiments, the insulin is administered in an amount of about 8 U/kg/day. In some embodiments, the insulin is administered in an amount of about 10 U/kg/day.

In some embodiments, the insulin for use in the methods of the present disclosure is provided in a composition, in which the insulin is microencapsulated within a matrix of maltodextrin (MD). In some embodiments, the insulin is provided in the form of particles, wherein the particles have a maltodextrin core and a drug layer of human insulin.

The term "about" in reference to a numerical value stated herein is to be understood as the stated value +/−10%.

The terms "clinical efficacy" and "clinically effective" refer to a treatment that results in a statistically significant therapeutic effect. By "statistically significant" it is meant that the result was unlikely to have occurred by chance. Statistical significance can be determined by any method known in the art. Commonly used measures of significance include the p-value, which is the frequency or probability with which the observed event would occur, if the null hypothesis were true. If the obtained p-value is smaller than the significance level, then the null hypothesis is rejected. In simple cases, the significance level is defined at a p-value of 0.05 or less.

Thus, according to some embodiments, administering insulin to a subject according to the methods of the present disclosure provides a statistically significant therapeutic effect in the reduction of gastric residuals of the subject. In some embodiments, administering insulin to a preterm or low birth weight infant according to the methods of the present disclosure provide a clinically effective means of reducing gastric residuals in preterm or low birth weight infants. Accordingly, in some embodiments, administering insulin to a preterm or low birth weight infant according to the methods of the present disclosure provide a clinically effective means of treating delayed gastric emptying in preterm or low birth weight infants. In some embodiments, the statistically significant therapeutic effect is determined based on one or more standards or criteria provided by one or more regulatory agencies in the United States, e.g., FDA or other countries. In certain embodiments, the statistically significant therapeutic effect is determined based on results obtained from regulatory agency approved clinical trial set up and/or procedure.

In some embodiments, the statistically significant therapeutic effect is determined based on a patient population of at least 10, 20, 30, 40, 50, 60, 70, 80, 90, 100, 200, 300, 400, 500, 600, 700, 800, 900, 1000 or 2000. In specific embodiments, the statistically significant therapeutic effect is determined based on a patient population that is appropriate for an orphan drug indication. In some embodiments, the statistically significant therapeutic effect is determined based on data obtained from randomized and double-blinded clinical trial set-up. In some embodiments, the statistically significant therapeutic effect is determined based on data with a p-value of less than or equal to about 0.07, 0.06, 0.05, 0.04, 0.03, 0.02 or 0.01. In some embodiments, the statistically significant therapeutic effect is determined based on data with a confidence interval greater than or equal to 95%, 96%, 97%, 98% or 99%. In some embodiments, the statistically significant therapeutic effect is determined on approval of Phase II or III clinical trial of the methods provided by the present invention, e.g., by FDA in the US.

In some embodiments, the clinically-effective or statistically significant therapeutic effect is determined by a randomized double blind clinical trial of a patient population of at least 10, 20, 30, 40, 50, 60, 70, 80, 90, 100, 200, 300 or 350, or a patient population appropriate for an orphan drug indication, treated with enteral administration of insulin at a dosing level described herein. For example, in some embodiments, the statistically significant therapeutic effect is determined by a randomized clinical trial of a patient population using, for example, gastric residuals as a readout for gastric emptying.

In general, statistical analysis can include any suitable method permitted by a regulatory agency, e.g., FDA in the US or China or any other country. In some embodiments, statistical analysis includes non-stratified analysis, log-rank analysis, e.g., from Kaplan-Meier, Jacobson-Truax, Gulliken-Lord-Novick, Edwards-Nunnally, Hageman-Arrindel and Hierarchical Linear Modeling (HLM) and Cox regression analysis.

The term "modulating" includes "increasing" or "enhancing," as well as "decreasing" or "reducing," typically in a statistically significant or a physiologically significant amount as compared to a control. An "increased" or "enhanced" amount is typically a "statistically significant" amount, and may include an increase that is about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.2, 3.4, 3.6, 3.8, 4.0, 4.2, 4.3, 4.4, 4.6, 4.8, 5, 6, 7, 8, 9, 10, 15, 20, 30, 40, 50 or more times (e.g., 100, 200, 500, 1000 times) (including all integers and decimal points and ranges in between and above 1, e.g., 5.5, 5.6, 5.7. 5.8, etc.) the amount produced by a control (e.g., the absence or lesser amount of a compound, a different compound or treatment), or the amount of an earlier time-point (e.g., prior to treatment with a compound). A "decreased" or "reduced" amount is typically a "statistically significant" amount, and may include a 1%, 2%, 3%, 4%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95%, or 100% decrease (including all integers and decimal points and ranges in between) in the amount or activity produced by a control (e.g., the absence or lesser amount of a compound, a different compound or treatment), or the amount of an earlier time-point (e.g., prior to treatment with a compound)

The following examples are presented in order to more fully illustrate some embodiments of the disclosure. They should, in no way be construed, however, as limiting the broad scope of the disclosure. One skilled in the art can readily devise many variations and modifications of the principles disclosed herein without departing from the scope of the disclosure.

EXAMPLES

Example 1. Effect of Insulin on Gastric Emptying Rate of Preterm Infants

Evaluation of gastric residuals (GR) is used in neonatal intensive care units to measure the volume of milk remaining in the stomach at a variable time after a feeding, and as an indicator of gastric emptying (GE).

A Multi-center, two arms, randomized, double-blinded placebo controlled study was conducted to evaluate the effect of insulin-enriched infant formula on preterm infants. The insulin was given within a liquid infant formula with insulin concentration of 400 µU/ml. The study primary goal was to determine whether insulin supplement within the basic preterm oral formula enhances gastric emptying. The gastric emptying was evaluated by the reduction in the amount of gastric residual of the preterm infants.

Study Design

Parents of eligible preterm infants who meet the study criteria described hereinbelow were invited to participate in the study following signing of an Informed Consent Form (ICF). The infants were hospitalized in the neonatal hospital ward in the same manner as preterm infants whose parents elected not to participate in the study. The infants were randomly assigned to one of two treatment groups: the study product containing insulin as a test group and Placebo supplement as a control group. The parents, the medical team treating the infants and the study monitor were blinded to the treatment arm. From study day 1, the infants in the test group received insulin mixed with the ready to feed (RTF) preterm Materna formula and the control group received a placebo supplement mixed with the same RTF preterm Materna formula.

33 preterm infants, aged up to 7 days old, born between 26-33 weeks of pregnancy, weighing over 750 grams, who are free from high index suspicion for infection showing stable condition were enrolled into this study.

Randomization was carried by block design. Each site received a randomly selected block of size 4 in which consecutive infant ID numbers was allocated to either one of the two groups (treatment/placebo). Once enrollment of the four infants block is completed, the site received an additional block.

One subject was withdrawn due to health complications; 32 subjects were included in the analyses, 15 males and 17 females aged between 1-7 days old.

Inclusion Criteria

The following criteria had to meet in order to be included in the study:
 1. Pre-term infants born after 26-33 weeks gestation. Gestational age matching (±2 weeks) between maternal dates and early antenatal ultrasound.

2. Birth weight≥750 gr.
3. Postnatal age≤7 days.
4. Fraction of inspired oxygen≤0.60 at enrollment.
5. The infant is in a cardiovascular stable condition.
6. No breast feeding after study day 1.
7. No heart and chest compression or any resuscitation drugs given to the infant during delivery
8. Informed consent form signed by parents or legal guardian.

Exclusion Criteria

Infants who meet one or more of the following criteria were excluded from the study:
1. Pre-term infants age <26 or >33 weeks gestation. Gestational age matching (±2 weeks) between maternal dates and early antenatal ultrasound.
2. Birth weight<750 grams.
3. Postnatal age>7 days.
4. Fraction of inspired oxygen>0.60 at enrollment.
5. The infant is in cardiovascular instability.
6. Breast feeding after study day 1.
7. Major congenital malformation—Infants with genetic metabolic or endocrine disorder diagnosed before enrollment (including disorders diagnosed after enrollment but are known to be congenital).
8. High index of suspicion of infection before enrollment.
9. Infant developing necrotizing enterocolitis or is suspected of having necrotizing enterocolitis.
10. Maternal diabetes.
11. The infant is treated with Insulin.
12. Nil per os (NPO) for any reason at the study entry.
13. Heart and chest compression or any resuscitation drugs given to the infant during delivery.
14. Participation in another clinical study.

Trial Products

The study products included the insulin composition disclosed herein and placebo. The insulin composition is intended to be mixed with 90 ml ready to feed (RTF) preterm infant formula (manufacturer: Nestle Germany, importer: Materna Laboratories, Israel). Once the insulin is added to the formula, the formula has the concentration of 400 µU Insulin/ml formula.

The insulin composition comprises three components:

(a) Human insulin which is a large protein (5,800 Daltons) composed of two polypeptide chains joined by two disulfide bonds. Insulin is a natural health promoting component present in mammalian milk, at concentrations of nanogram per milliliter. Insulin is also classified as a peptide hormone when injected in therapeutic dosages by individuals diagnosed with diabetes mellitus.

(b) Maltodextrin which is a mixture of polysaccharides, produced by the partial hydrolysis of starch. Maltodextrin is commonly used as a component in infant's formula and dissolves immediately in liquid.

(c) Vitamin C or L-ascorbic acid which is an essential nutrient for humans. In living organisms, ascorbate is an anti-oxidant, since it protects the body against oxidative stress, and is a cofactor in several vital enzymatic reactions. In the insulin formulation vitamin C is used as an indicator for insulin oxidation.

The placebo consists of Maltodextrin and vitamin C.

The insulin composition was used according to study definitions and feeding protocol only. Formula administration was begun at study day 1 and continued throughout the following 28 days or discharge day if achieved prior to day 28.

The insulin composition was kept at room temperature and out of reach of children. insulin composition has no contraindications.

Product Administration

The content of the study sachet (containing 0.5 g insulin composition/placebo; the insulin composition containing total of about 36 mU of insulin), marked per infant, was added by the neonatal intensive care unit (NICU) nurses into a 90 ml glass bottle of RTF premature infants Materna formula, right before each meal. Once added, the bottle was closed and shaken well to insure the additive has completely dissolved. The infants received a new 90 ml glass bottle+ additive per meal. Standard feeding bottles and nipples were used. Once the infant finished the meal, the left over formula was kept in the glass bottle for 24 hours for lab use only. If the infant was found to be stable and well, the bottle was discarded, otherwise the sponsor was informed and collected the bottle for examination.

The gastric residual amount was measured after every meal.

Twin Pair Study

Figure 1:
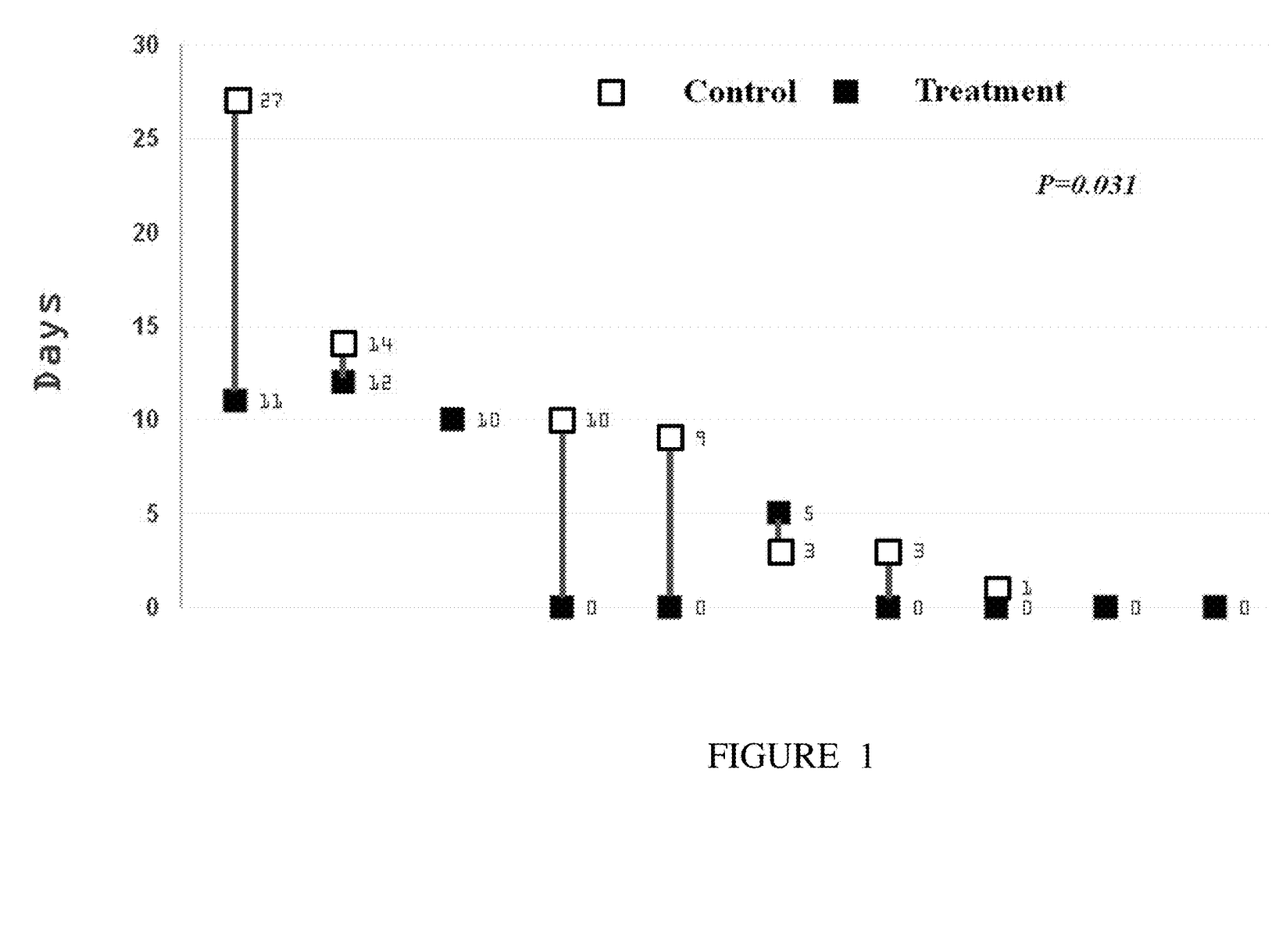
FIG. 1 shows the effect of insulin treatment on the number of days until preterm infants reach gastric residuals of less than 2 ml/Kg body weight. The experiment was conducted on twin pairs. Each column represents one twin pair in which one was treated with insulin and the other served as control.
Figure 2:
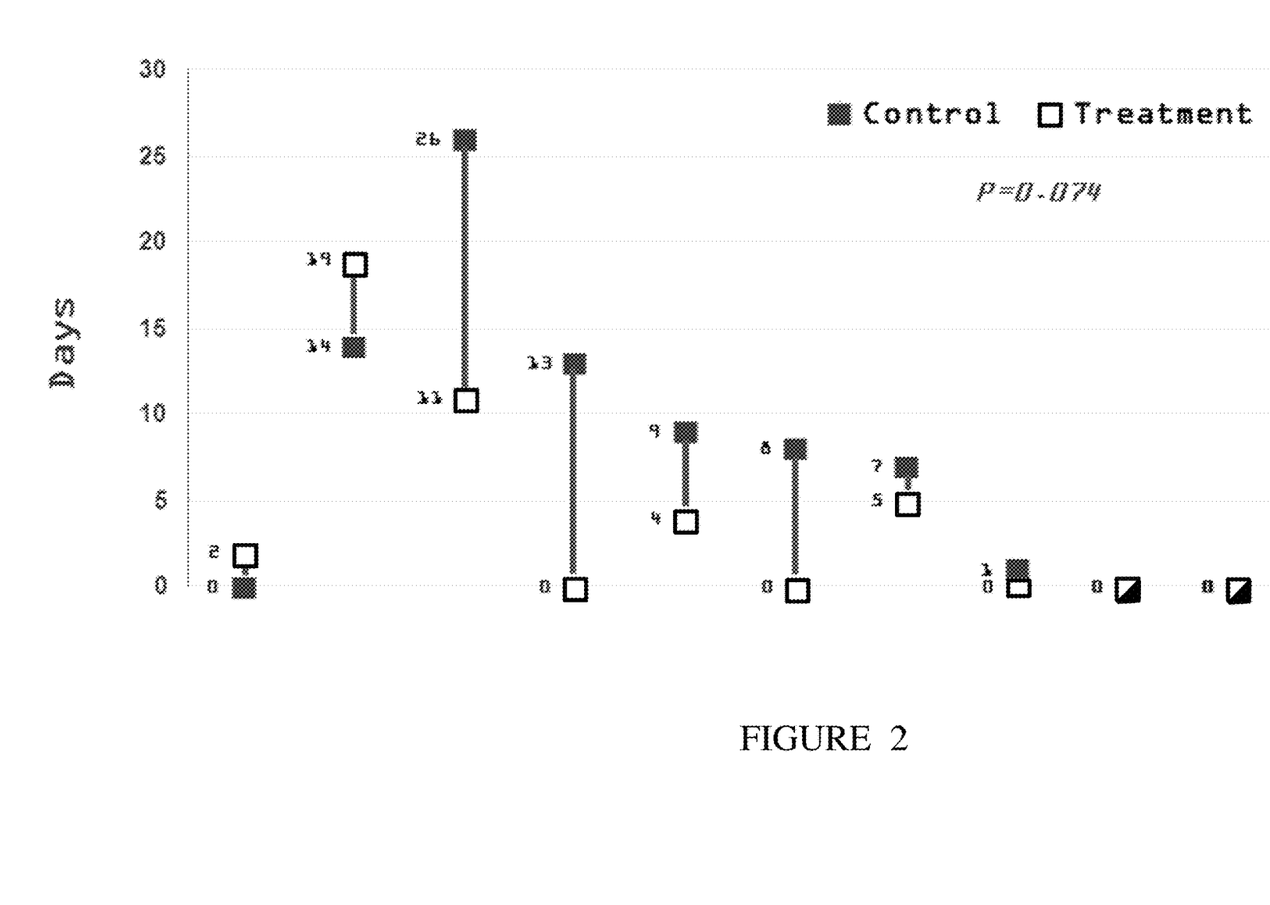
FIG. 2 shows the effect of insulin treatment on the number of days until preterm infants reach gastric residuals of 0 ml/Kg body weight. The experiment was conducted on twin pairs. Each column represents one twin pair in which one was treated with insulin and the other served as control.

Twin pairs, treated with insulin as described above, were examined for number of days until gastric residual measurements reached less than 0 ml/kg body weight (FIG. 2 and Table 1) or 2 ml/kg (FIG. 1 and Table 2). Twin infants treated with insulin reached gastric residuals of less than 2 ml/kg or 0 ml/kg earlier than their control infant twin in most twin pairs (FIG. 1 (p=0.031) and FIG. 2 (p=0.074), respectively). Tables 1 and 2 summarize the results. The enteral administration of insulin strikingly provided a statistically significant improvement in the number of days until gastric residuals reached 0 mg/kg body weight, or <2 ml/kg body weight, relative to control treated infants.

TABLE 1

Number of days until gastric residuals reached 0 ml/Kg body weight.

|  | Control (C) | Treatment (T) |  |
|---|---|---|---|
| Average | 7.8 | 4.1 | P = 0.074 |
| (SE) | (2.8) | (2.2) |  |
| Median | 8.0 | 0.0 |  |
| (range) | (0; 26) | (0; 19) |  |

TABLE 2

Number of days until gastric residuals reached < 2 ml/Kg body weight.

|  | Control (C) | Treatment (T) |  |
|---|---|---|---|
| Average | 7.7 | 3.8 | P = 0.031 |
| (SE) | (2.7) | (1.7) |  |
| Median | 6 | 0 |  |
| (range) | (0; 27) | (0; 12) |  |

Singleton Study

Figure 3:
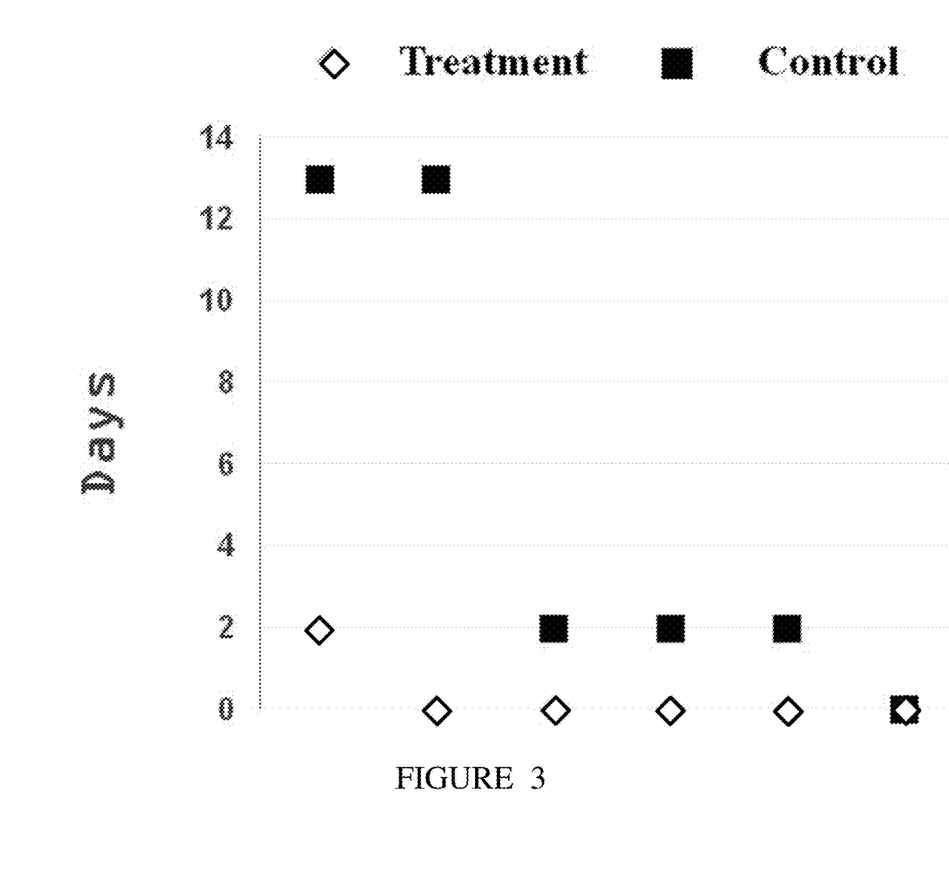
FIG. 3 shows the effect of insulin treatment on the number of days until preterm infants reach gastric residuals of less than 2 ml/Kg body weight. Each column represents two singletons, wherein one received insulin orally and the other served as control.

Singletons were examined for number of days until gastric residual measurements reached less than 2 ml/kg body weight (FIG. 3) and until no gastric residuals were emitted (Table 3). As shown in FIG. 3, singletons treated with insulin reached gastric residuals of less than 2 ml/kg earlier than the control (P=0.121).

Singletons treated with insulin reached no gastric residuals (0 ml/kg) earlier than their control singletons (Table 3; P=0.021). Thus, the enteral administration of insulin to the infants achieved a statistically significant improvement in the number of days until no gastric residuals were emitted, relative to control treated subjects.

TABLE 3

Number of days until no gastric residuals are emitted.

| Control | | Treatment | |
|---|---|---|---|
| Infant no. | days | Infant no. | days |
| 1 | 18 | 1 | 0 |
| 2 | 2 | 2 | 0 |
| 3 | 9 | 3 | 2 |
| 4 | 0 | 4 | 0 |
| 5 | 2 | 5 | 0 |
| 6 | 15 | 6 | 0 |
| Median (range) | 5.5 (0-18) | Median (range) | 0.0 (0-2) |

The results presented in examples 1 and 2 clearly demonstrate the significant beneficial effect of insulin on the gastric emptying rate of low birth weight infant. No deleterious effects resulting from the insulin administration were observed.

Example 2

To further examine the effect of insulin treatment on gastric emptying, patients suffering from gastroparesis are treated with insulin according to the disclosure, and a breath test is conducted according to Cappello G et al. (Am J Gastroenterol. 2000 November; 95(11):3097-100). Gastroparesis patients are randomized into two groups; one group is treated with daily oral dosage of 1 U/Kg body weight per/day insulin for a week, and the other group serves as control. At the day of the experiment, patients are fed with non-radioactive stable isotope $^{13}C$ substrate, which is dissolved in solid test meals (i.e., $^{13}C$-octanoic acid in egg yolk). The appearance of $^{13}CO_2$ in the breath is then measured. Breath samples are taken at baseline and every 30 min over a period of 240 min. Measurement of exhaled $^{13}CO_2$ is performed by mass spectrometry or infrared spectroscopy. A delay in the appearance of $^{13}CO_2$ in breath samples is due to a reduced solid transit pace between the stomach and the duodenum, i.e. gastric emptying becomes the rate-limiting step when the substrate is rapidly absorbed.

The foregoing description of the specific embodiments will so fully reveal the general nature of the disclosure that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the disclosure.

The invention claimed is:

1. A method for promoting gastric emptying in a subject in need thereof, comprising the step of enterally administering an effective amount of insulin or a composition comprising same to the subject, thereby promoting the gastric emptying in said subject, wherein the subject is a low birth weight infant, wherein promoting the gastric emptying is defined as reaching gastric residuals of less than 2 ml/kg body weight in 4 days or fewer, and wherein the method comprises administering to the subject insulin in an amount from about 200 µU/mL to about 4,000 µU/mL.

2. The method of claim 1, wherein the subject is a preterm infant.

3. The method of claim 1, wherein the subject was born at a gestational age of 26-32 weeks.

4. The method of claim 3, wherein the subject was born at a gestational age of 26-28 weeks.

5. The method of claim 3, wherein the subject was born at a gestational age of 29-32 weeks.

6. The method of claim 1, wherein the number of days to reach gastric residuals of 0 ml/kg body weight is 5 days or fewer.

7. The method of claim 1, wherein the number of days to reach gastric residuals of 0 ml/kg body weight is 2 days or fewer.

8. The method of claim 1, wherein the method comprises administering the insulin in an amount from about 400 µU/mL to about 2000 µU/mL.

9. The method of claim 1, wherein the method comprises administering the insulin in an amount of about 400 µU/mL.

10. The method of claim 1, wherein the method comprises administering the insulin in an amount of about 2000 µU/mL.

11. The method of claim 1, wherein the insulin is in a matrix comprising maltodextrin.

12. The method of claim 2, wherein the insulin is mixed with an infant formula to form an insulin-enriched formula.

13. The method of claim 12, wherein the insulin-enriched formula comprises insulin at a concentration range of from about 400 µU/mL to about 2000 µU/mL.

14. The method of claim 12, wherein the insulin-enriched formula comprises insulin at a concentration of about 400 µU/mL.

15. The method of claim 12, wherein the insulin-enriched formula comprises insulin at a concentration of about 2000 µU/mL.

16. The method of claim 1, wherein the insulin is selected from the group consisting of human insulin and bovine insulin.

17. The method of claim 1, wherein the insulin is selected from the group consisting of recombinant insulin and synthetic insulin.

18. The method of claim 1, wherein the insulin is administered via a route selected from normal feeding and a feeding tube.

19. The method of claim 1, wherein the insulin is administered for up to 28 days.

20. The method of claim 2, wherein the infant is in a hospital during administration of the insulin, and wherein the insulin is administered until the infant is discharged from the hospital.

21. The method of claim 1, wherein the administration of an effective amount of insulin or a composition comprising the same provides a statistically significant therapeutic effect in promoting the gastric emptying in the subject.

22. The method of claim 1, wherein the composition is a nutritional composition.

23. The method of claim 1, wherein the method comprises administering a total amount of insulin to the subject of about 0.005 U/kg/day to about 0.5 U/kg/day.

* * * * *